United States Patent [19]

Boman et al.

[11] Patent Number: 5,096,886

[45] Date of Patent: Mar. 17, 1992

[54] ANTIBACTERIAL PORCINE POLYPEPTIDES

[75] Inventors: Hans G. Boman, Odengaten; Hans Jörnvall, Vallstigen; Jong-Youn Lee, Stockholm; Viktor Mutt, Solua, all of Sweden

[73] Assignees: Kabigen AB; Skandigen AB, both of Stockholm, Sweden

[21] Appl. No.: 531,110

[22] Filed: May 31, 1990

[30] Foreign Application Priority Data

Jun. 16, 1989 [SE] Sweden ............... 89021869

[51] Int. Cl.$^5$ ............ A61K 37/02; C07K 7/10; C07K 3/02; C07K 13/00
[52] U.S. Cl. ............................. 514/12; 530/324
[58] Field of Search .................... 514/12; 530/324

[56] References Cited

U.S. PATENT DOCUMENTS 4,705,777 11/1987 Lehrer et al. .................. 514/12
4,810,777 3/1989 Zasloff ........................... 530/326
4,962,277 10/1990 Cuervo et al. .................. 514/14

OTHER PUBLICATIONS

Hultmark et al., "Insect Immunity", *The EMBO Journal* 2: 571–576, 1983.

*Primary Examiner*—John Doll
*Assistant Examiner*—Stephen Walsh
*Attorney, Agent, or Firm*—Burns, Doane, Swecker & Mathis

[57] ABSTRACT

A polypeptide having bactericidal activity, particularly against gram-negative bacteria, has been isolated from pig intestine. The porcine cecropin has the amino acid sequence: H$_2$N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COOH. Pharmaceutical compositions containing such poypeptides, or functional derivatives thereof, are useful in therapeutic and prophylactic methods for inhibiting bacterial growth.

22 Claims, No Drawings

ANTIBACTERIAL PORCINE POLYPEPTIDES

The present invention relates to new polypeptides having bactericidal activity in that they are capable of killing certain bacteria, particularly gram-negative ones. The invention also covers pharmaceutical compositions and methods of use for the inhibition of bacterial growth.

The small intestine is an important endocrine organ and a number of physiologically active peptides have been initially isolated from porcine tissue (Mutt, V., Chemica Scripta 26B, 191-207 (1986)). During normal healthy conditions, the upper part of the small intestine contains few bacteria. Below the duodenum the concentration of bacteria progressively increases until the maximum, $10^{11}$ bacteria per g of feces, is reached in the large intestine. It is remarkable that such a mass of bacteria can coexist with a delicate host organ. Small basic peptides called cecropins play an important role in inset immunity (Boman, H. G. & Hultmark, D., D. Ann. Rev. Microbiol. 41, 103-126 (1987)) and structurally unrelated peptides called magainins (Zasloff, M., Proc. Natl. Acad. Sci. U.S.A., 84, 5449-5453 (1987)) protect the frog skin from infections. Another group of antibacterial peptides, the definsins were first isolated from mammalian granulocytes (Selstedt, M. E., Szklarek, D. & Lehrer, R. I. Infect. Immun. 45, 150-154 (1984)) and neutrophils (Selstedt, M. E., Brown, D. M., DeLange, R. J., Harwig, S. S. & Lehrer, R. I., J. Biol. Chem. 260, 4579-4584 (1985)) and recently also from insects (Matsuyama, K. & Natori, S. J. Biol. Chem. 263, 17112-17116 (1988); Lambert, J. et al. Proc. Natl. Acad. Sci. U.S.A. 86, 262-266 (1989)). In addition, bovine neutrophils have been found to contain bactenecins (Romeo, D., Skerlavaj, B., Bolognesi, M & Gennaro, R. J. Biol. Chem. 263, 9573-9575 (1988), another small basic peptide. Both definsins and bactenecins contain one or more disulfide bridges while cecropins and magainins are cysteine-free.

The present invention has for an object to provide new bactericidal polypeptides capable of inhibiting bacterial growth, in particular the growth of gram negative bacteria. In this disclosure the term "inhibiting" may include killing of bacteria.

Another object of the invention is provide compositions containing as an active constituent such polypeptides.

Yet another object of the invention is to provide a method of treatment directed to inhibition of bacterial growth in animals, in particular mammals including man.

For these and other objects which will be clear from the following disclosure the invention provides a polypeptide having the amino acid sequence: H₂N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COOH, and the invention also includes functional derivatives such as a few conservative amino acid replacements and the C-terminal amide. The amidated form is the better antibiotic (Example 3).

The polypeptide of the present invention and its functional derivatives are all therapeutically useful, particularly as antibacterial agents. Thus, they are capable of inhibiting growth of bacteria, in particular gram-negative bacteria making them useful for different therapeutic purposes. This will be further illustrated by specific examples which are given below.

The active polypeptide according to the present invention can be formulated for use in human or veterinary medicine for therapeutic or prophylactic use. The active preparations are normally administered orally, reactally or by injection in the form of pharmaceutical preparation or composition comprising the active constituents in combination with a pharmaceutically acceptable carrier which may be solid, semi-solid or liquid, or contained in a capsule, such as when orally administrered. As examples of pharmaceutical preparations there may be mentioned tablets, drops, solutions and suppositories. Usually, the active constituent constitutes the minor part of the preparation, such as from about 0.1 to about 50% thereof based on weight.

In order to prepare pharmaceutical compositions in the form of dose units for oral application the polypeptide of the invention can be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets or bodies for dragées.

By using several layers of the carrier or diluent tablets operating with slow release can be prepared.

Liquid preparations for oral application or for injection can be made in the form of elixirs, syrups or suspensions, for example solutions containing from 0.1 to 20% by weight of active substance, sugar and a mixture of ethanol, water, glycerol, propylene, glycol and possibly other additives of a conventional nature.

The dose by which the active constituent is administered may vary within wide limits and is dependent on different factors, such as the seriousness of the disorder, the age and the weight of the patient and can be adjusted individually.

The invention also covers a method for therapeutic treatment of animals, such as mammals including man, said method comprising the step of administering a polypeptide as described above or a functional derivative thereof in an amount capable of inhibiting bacterial growth in said animal.

The present invention will now be further exemplified by specific examples which, however, are not to be construed as limiting the scope of the invention otherwise than according to the appended claims.

EXAMPLE 1

Preparation of a peptide concentrate

A concentrate of thermostable intestinal peptides was prepared from pig small intestine essentially as described elsewhere (Mutt, V. Arkiv Kemi 15, 69-74 (1959); Mutt, V. in Gut Hormones (ed. Bloom, S. R.), pp 21-27, (Churchill Livingstone, Edinburg, 1978).

Briefly, the uppermost meter of the intestine was immersed for $8\pm1$ min into boiling water and then cooled on ice and frozen. The frozen material was minced and extracted at 0°-15° C. with 0.5M acetic acid for 12 h and the mixture filtered with suction (with the aid of "Hyflo Super-Cel", 30 g per liter suspension). Peptides were adsorbed from the filtrate to alginic acid and the alginic acid carrying the peptides was washed in turn with 0.005M HCl, 95% ethanol (to remove (fats) and 0.005M HCl again. The peptides were eluted with 0.2M ice-cold HCl and the pH of the eluate was brought to 3.5±0.1 with sodium acetate. Peptides were then precipitated by saturating the eluate with NaCl, and the precipitate was collected by suction filtration. The amount by weight of the precipitate (wet weight) is about one thousandth of that of the boiled intestinal tissue.

The concentrate was dissolved at room temperature to a 10% w/ve solution in water. Two volumes of 95% ethanol were added to the solution and the (apparent) pH (as measured with a glass electrode) of it was brought to 7.5±0.1 with NaOH (1M NaOH:EtOH 1:2). A precipitate formed and was removed by filtration. To the clear solution one volume of 95% ethanol precooled to −20° C. was added and the suspension was kept at this temperature for 24 h whereupon it was filtered. The peptides were recovered from the filtrate in aqueous solution and precipitated at pH 3.5±0.1 by saturation of the solution with NaCl. The precipitate, collected by suction filtration, weighed about 10% of that of the concentrate taken for its preparation. It was dissolved in 0.2M AcOH and chromatographed in this solvent on Sephadex G-25 fine. The second half by volume of the peptide containing eluate from this chromatography was saturated with NaCl and the precipitate collected by suction filtration. Its weight was about 40% of that of the peptide precipitate taken for this chromatography. It was dissolved in water, the pH of the solution was adjusted to 4±0.1 whereupon the peptides were reprecipitated with NaCl and the precipitate collected by suction (there was no significant difference in weight of the material before and after reprecipitation). The reprecipitated material was extracted with methanol (50 ml/g) and the MeOH-insoluble fraction was collected by suction filtration and washed on the filter with water. The ether was evaporated in vacuo. The weight of the dry material was about 15% of that of the peptide precipitate taken for extraction with MeOH.

EXAMPLE 2

Purification of concentrate

As a starting material for the purification there was used the concentrate resulting from Example 1. The concentrate (1.5 g) was dissolved in 80 ml ammonium formate, pH 6.4, and treated with 30 ml of DEAE Sepharose, batch-wise.

Step 1: Chromatography on CM-Sepharose CL-6B (56 ml column, equilibrated with 0.1M ammonium formate, pH 6.4). Elution was initially carried out with 0.1M ammonium formate (about 2100 ml) to a low extinction and then gradient elution was performed using 0.1-0.85M ammonium acetate, pH 5.2 (300+300 ml). The activity leaves as an integral peak having a maximum at 0.38M, specific activity 30-40 units/μg. (1 unit is defined as the activity of 1 ng of cecropin A.)

Step 2: Chromatography on an S Sepharose Fast Flow (26 ml column, equilibrated with 0.30M ammonium acetate, pH 5.2). The peak from Step 1 is diluted 1.3 times to about 0.3M and is applied to the column. Elution is initially carried out using 0.3M ammonium acetate (about 230 ml), then a gradient elution is performed with 3.30-0.50M ammonium acetate, pH 5.2 (300+300 ml). The activity leaves after the UV-material and the peak is eluated with 0.40M.

The peak material is freeze-dried, specific activity 200-400 units/μg.

Step 3: FPLC on PepRPC (C2/C18 column). The peak from Step 2 is dissolved in 0.1% TFA in water. The material is applied to the column equilibrated with 0.1% TFA. Elution is first carried out with 0.1% TFA unti $A_{214}$ decreases to the base line, and then complex gradient elution is performed: 0-5 min 0-29% $CH_3CN$, 5-45 min 19-48% $CH_3CN$, 45-50 min 48-100% $CH_3CN$. Many UV-peaks are observed but the activity is collected in 2-3 tubes eluted with 33% $CH_3CN$. The specific activity is estimated to be at least 700 units/μg.

Step 4: Rechromatography in FPLC on PepRPC. The peak from Step 3 is diluted twice with water and applied to the same column. Elution is first carried with 0.1% TFA unit $A_{214}$ decreases down to the base line, and then complex gradient elution is performed: 0-5 min 0-29% $CH_3CN$, 5-65 min 29-38% $CH_3CN$, 65-70 min 38-100% $CH_3CN$. Generally one UV-peak eluting with activity at 33% $CH_3CN$. Specific activity approximately 700-1200 units/μg.

The purified peptide resulting from Step 4 was subjected to sequence analysis and mass spectroscopy. The amino acid sequence give above was confirmed.

EXAMPLE 3

The polypetide obtained in Example 2 was tested for antibacterial activity against different bacteria, the activity being given as lethal concentrations in micromoles per liter (μM). The results from the experiments are given in Table 1 below.

TABLE 1

Antibacterial activities as lethal concentrations (μM) for two synthetic forms of porcine cecropin P1C1.

| Organism and strain | P1-NH$_2$ | P1-OH |
|---|---|---|
| *Escherichia coli* | | |
| K12, D21 | 0.3 | 0.4 |
| 853/67, O149, K88 | 0.9 | 0.6 |
| Bd2221/75, O8, K88 | 0.6 | 0.7 |
| Bd4462/84, O101, K99 | 0.7 | 0.8 |
| Bd4468/84, O64, K99 | 0.3 | 0.6 |
| *Salmonella typhimurium*, LT2 | 0.9 | 1.7 |
| *Acinetobacter calcoaceticus*, Ac11 | 0.2 | 0.5 |
| *Proteus vulgaris*, Pv11 | 5.7 | 12 |
| *Pseudomonas aeruginosa*, OT97 | 5.9 | 13 |
| *Bacillus megaterium*, Bm11 | 1.8 | 5.3 |
| *Streptococcus pyogenes* | 19 | 44 |
| *Staphylococcus aureus*, Cowan 1 | >490 | >520 |

The four last strains of *E. coli* were obtained from Olof Söderlind, SVA, Uppsala and they are clinical isolates that are pathogenic to piglets. Typing of O and K antigens are indicated after the strain number. Lethal concentration is the lowest concentration of cecropin that inhibits growth of the respective bacteria in thin agarose plates (see Hultmark, D. et al. EMCO J. 2, 571-576 (1983).

We claim:

1. Polypeptides having the amino acid sequence: H$_2$N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COOH, and functional derivatives thereof consisting of conservative amino acid replacements.

2. Polypeptides according to claim 1, in an underivatized form.

3. Polypeptides according to claim 1 in the form of an amide.

4. Polypeptides having the amino acid sequence: H$_2$N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COOH, and functional derivatives thereof consisting of comprising conservative amino acid replacements for therapeutic use.

5. Polypeptides having the amino acid sequence: H$_2$N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COOH, and functional derivatives thereof consisting of comprising conservative amino acid replacements for use as an antibacterial agent.

6. A pharmaceutical composition containing as an active constituent of the polypeptide according to claim 1 in an antibacterially effective amount together with a pharmaceutically acceptable carrier or diluent.

7. A pharmaceutical composition according to claim 6, wherein said carrier or diluent is acceptable for oral, intramuscular, intravenous or subcutaneous administration.

8. A method for inhibiting bacterial growth in animals, comprising the step of administering a polypeptide according to claim 1 in an inhibitory amount.

9. A method according to claim 8 for intestinal use comprising oral administration of said polypeptide in a slow release dose form.

10. A method according to claim 8, comprising administration by injection of said polypeptide in an injectable dose form.

11. A polypeptide having the amino acid sequence: H$_2$N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COOH for therapeutic use.

12. A polypeptide having the amino acid sequence: H$_2$N-Ser-Trp-Leu-Ser-Lys-Thr-Ala-Lys-Lys-Leu-Glu-Asn-Ser-Ala-Lys-Lys-Arg-Ile-Ser-Glu-Gly-Ile-Ala-Ile-Ala-Ile-Gln-Gly-Gly-Pro-Arg-COONH$_2$ for therapeutic use.

13. A pharmaceutical composition containing as an active constituent the polypeptide according to claim 2 in an antibacterially effective amount together with a pharmaceutically acceptable carrier or diluent.

14. A pharmaceutical composition containing as an active constituent the polypeptide according to claim 3 in an antibacterially effect amount together with a pharmaceutically acceptable carrier or diluent.

15. A method for inhibiting bacterial growth in animals, comprising the step of administering a polypeptide according to claim 2 in an inhibitory amount.

16. A method for inhibiting bacterial growth in animals, comprising the step of administering a polypeptide according to claim 3 in an inhibitory amount.

17. A method according to claim 8, wherein said animal is a mammal.

18. A method according to claim 17, wherein said mammal is a man.

19. A method according to claim 15, where said animal is a mammal.

20. A method according to claim 19, wherein said mammal is a man.

21. A method according to claim 16, wherein said animal is a mammal.

22. A method according to claim 21, wherein said mammal is a man.

* * * * *